(12) United States Patent
Commarieu et al.

(10) Patent No.: US 6,235,198 B1
(45) Date of Patent: *May 22, 2001

(54) PROCESS FOR PURIFICATION OF DIMETHYL SULPHOXIDE (DMSO)

(75) Inventors: Annie Commarieu, Courbevoie; Francis Humblot, Lanneplaa, both of (FR)

(73) Assignee: Elf Aquitaine Exploration, Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/078,414

(22) Filed: May 14, 1998

(30) Foreign Application Priority Data

May 15, 1997 (FR) .................................................. 97 05967

(51) Int. Cl.[7] .......................... C07C 315/06; B01D 15/08
(52) U.S. Cl. .......................... 210/638; 210/660; 210/681; 568/37
(58) Field of Search .............................. 568/37; 210/638, 210/660, 681, 687, 688

(56) References Cited

U.S. PATENT DOCUMENTS 5,990,356 * 11/1999 Commarieu .......................... 210/638
6,020,530 * 2/2000 Commarieu .......................... 210/638
6,123,850 * 9/2000 Commarieu .......................... 210/638

OTHER PUBLICATIONS

Alan M. Phipps, "Anion Exchange in Dimethyl Sulfoxide", *Analytical Chemistry* 40(12):1769–1773 (1968).

Copy of French Search Report dated Jan. 28, 1998.

Derwent Abstract of WO9629334 Sep. 26, 1996.

UK Search Report dated Jul. 30, 1998.

Chaudron, Chimie Analytique 53(5):310–314 (1971) [Includes English Abstract].

* cited by examiner

*Primary Examiner*—Ernest G. Therkorn
(74) *Attorney, Agent, or Firm*—Smith, Gambrell & Russell

(57) ABSTRACT

To purify a dimethyl sulphoxide (DMSO), it is placed in contact with a plurality of cation exchange resins at least one of which is a resin of sulphonic type in —$SO_3H$ or —$SO_3NH_4$ form, it being possible for the other or others to be of chelating type. The DMSO thus obtained has an iron cation content lower than 1 ppb and a sodium cation content lower than 2 ppb.

5 Claims, No Drawings

PROCESS FOR PURIFICATION OF DIMETHYL SULPHOXIDE (DMSO)

FIELD OF THE INVENTION

The present invention relates to a process for the purification of dimethyl sulphoxide (DMSO) and to the DMSO thus purified.

BACKGROUND OF THE INVENTION

The DMSO currently available on the market is a product which is already of good purity. Its commercial specifications are generally:

| | |
|---|---|
| purity | ≧99.7% by chromatography |
| acidity | ≦0.04 mg KOH/g by potentiometry |
| crystallization point | ≦18.1° C. |
| visual appearance | ≦clear |
| water content | ≦0.15% |
| colour (APHA) | ≦10 |

Patent FR 2 014 385 describes a process for the preparation of purified DMSO using an ion exchange resin. In both examples of this patent a strongly basic resin of the Amberlite IR-A 400 or Merck III type is employed to treat dimethyl sulphide/DMSO/10% sulphuric acid ternary mixtures. In fact, in this known process the purification seems to be essentially brought about by a fractional distillation of an aqueous solution of DMSO treated beforehand with an anion exchanger.

Analyses of trace metals have now been performed on a number of samples of commercial DMSO from various sources. These analyses are reported in Table 1.

The sodium, iron, potassium, calcium, chromium, copper, nickel and zinc concentrations were measured using ICP (plasma torch—atomic emission spectrometry, Perkin Elmer instrument, Optima 3000 model) and are expressed in ppb (1 ppb=1 part by weight per thousand million=1 $\mu$g per kg).

The list of the metallic elements which appears in Table 1 is not exhaustive in respect of the metallic elements present in these samples.

TABLE 1

| | Metal cations | | | | | | | |
|---|---|---|---|---|---|---|---|---|
| Sample | Na | Fe | K | Ca | Cr | Cu | Ni | Zn |
| 1 | 40 | 13 | 60 | 20 | 2 | 10 | 8 | 10 |
| 2 | 39 | 60 | 3 | 13 | 13 | <2 | 18 | 3 |
| 3 | 30 | 40 | 3 | 20 | 12 | <2 | 15 | 3 |
| 4 | 30 | 40 | 3 | 14 | 13 | <2 | 15 | 3 |
| 5 | 30 | <1 | 20 | 25 | <2 | <2 | <3 | <3 |
| 6 | 70 | 90 | 65 | 55 | 15 | 2 | 25 | 60 |
| Detection limit | 2 | 1 | 3 | 2 | 2 | 2 | 3 | 3 |

For some applications, as for example in electronics or in pharmacy, the DMSOs analysed above contain too many metallic impurities. A DMSO containing less than 10 ppb of each alkali and alkaline-earth metal and metal contaminant would generally be necessary for most of the uses in the abovementioned two technical fields.

DESCRIPTION OF THE INVENTION

The objective of the present invention is to find a process for purification of commercial DMSO which is already of good purity, the latter being nevertheless insufficient for some applications.

Ion exchange by making use of resins is a technique which is widely employed in the case of aqueous media and particularly allows deionized water to be obtained. The exchange of anions in a liquid DMSO medium of low water content has already been carried out by Alan M. Phipps, Anal. Chem. 40(12) pp. 1769–1773, 1968, with the aim of measuring the quantities of anions bound to the resin in experimental conditions approaching thermodynamic equilibrium.

The subject-matter of the invention is now a process for purification of dimethyl sulphoxide in order to decrease its content of alkali and alkaline-earth metal and metal cations, characterized in that it consists essentially in placing the DMSO to be purified in contact with at least two cation exchange resins at least one of which is a resin of sulphonic type, it being possible for the other (or the others) to be of chelating type.

A DMSO of low water content is advantageously treated, this content being preferably lower than or equal to 0.15% by weight relative to the total weight.

In accordance with the present invention any cation $M^{n+}$ (n having a value from 1 to 4) is retained and exchanged with $H^+$ protons or $NH_4^+$ cations originating from the resins employed in the acidic form or in the ammonium form.

A highly efficient purification of virtually anhydrous DMSO can be obtained by the combined use of a resin of chelating type which possesses, for example, aminophosphonic or iminodiacetic groups, which is effective for exchanging iron and metals with a multiple charge ($M^{n+}$, n=2, 3 and 4) and a resin of sulphonic type, which is effective for exchanging sodium and single-charge ions.

The cationic resins employed are preferably based on a polystyrene-divinylbenzene copolymer. These resins, in fact, have a backbone which withstands chemical attacks and in particular, they do not dissolve in DMSO.

The contact of the DMSO to be purified with the resins takes place at a temperature ranging from 18.45° C. (melting point of DMSO) to 120° C. (heat stability limit temperature of the resins). This temperature is advantageously between 19 and 80° C., preferably between 20 and 50° C.

The DMSO to be purified may be placed in contact with a mixture of the various resins or successively with each of the various resins.

The operation may be carried out noncontinuously (batchwise) or continuously in the conditions and equipment which are well known to a person skilled in the art. The separation of the purified DMSO from the resins can take place using any suitable known means, especially by filtration, percolation or centrifuging.

Iron and sodium have been adopted as tracer elements and indicators of the general content of alkali and alkaline-earth metal and metal cations, to define the quality of the DMSO capable of being obtained purified by the process according to the invention.

This purified DMSO is characterized in that it has an Fe cation content lower than or equal to 1 ppb and an Na cation content lower than or equal to 2 ppb, the respective limits of detection of the analysis method using plasma torch—atomic emission spectrometry.

EXAMPLES

The invention will be understood bette with the aid of the following experimental part describing an example of embodiment of the present invention.

Experimental Part

I. Method of Analysis:

ICP(plasma torch—atomic emission spectrometry) was employed for analysing the traces of metals in the DMSO: the sample is introduced into a plasma torch, the various elements present are excited and emit photons whose energy is characteristic of the element, since it is defined by the electron structure of the element in question. A Perkin Elmer instrument (Optima 3000 DV model) was employed routinely.

II. Methodology:

Principle: the trace metals are in $M^{n+}$ form. On passing the DMSO over two cation exchange resins, themselves in $H^+$ form, the Mn ions in solution are replaced with n $H^+$.

III. Test:

Principle: to simplify the analyses, sodium and iron were chosen as tracers representing all the metallic impurities present in the DMSO.

Sodium is characteristic of the atmospheric and accidental contamination (dust, environment), and iron is characteristic of the contamination that can originate from the process (unit made of stainless steel).

DMSO doped with 1000 ppb of iron and 1000 ppb of sodium was successively placed in contact with two cation exchange resins, in $H^+$ form (2 g of each resin per 100 g of DMSO) at 25° C. After a first cationic exchange with a resin of chelating type the DMSO was separated from the solid by filtration on a polyethylene sinter of 70 μm porosity and was then placed in contact with a resin of sulphonic type. Samples of DMSO were taken in the course of time during each of the stages, to follow the changes in the iron and sodium concentrations.

Amberlyst®35 resin marketed by Rohm & Haas was employed as resin of sulphonic type and the aminophosphonic resin S940 from Purolite as chelating resin. These resins were pretreated to obtain the $H^+$ form in the following manner: 540 ml of 5% HCl are passed through 90 ml of resin at a flow rate which is constant and such that the operation takes 30 to 45 minutes. After having been rinsed with deionized water until the water coming out is neutral, the resin was dried by being suspended in methanol and vacuum evaporation in the rotary evaporator (90° C., 2000 Pa) until a constant weight was observed.

The iron and sodium contents as a function of the time for the first and second exchange are collated in Table 2.

TABLE 2

|  | Time (min) | Fe (ppb) | Na (ppb) |
| --- | --- | --- | --- |
| Purolite ®S940 | 0 | 1390 | 1330 |
| resin | 30 | 64 | 1120 |
|  | 60 | <1 | 960 |
|  | 90 | <1 | 880 |
|  | 120 | <1 | 800 |
| Amberlyst ®A35 | 5 | <1 | <2 |
| resin | 30 | <1 | <2 |
|  | 60 | <1 | <2 |
|  | 120 | <1 | <2 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process for purification of dimethyl sulphoxide (DMSO) to decrease its content of alkali and alkaline-earth metal and metal cations, comprising placing the DMSO to be purified in contact with at least two cation exchange resins at least one of which is a resin which is sulphonic, and a second resin which optionally is a chelating resin, these resins being employed in the acidic or ammonium form.

2. Process according to claim 1, wherein a DMSO of low water content is treated, this content being lower than or equal to 0.15% by weight relative to the total weight.

3. Process according to claim 1, wherein each resin is based on a polystyrene-divinylbenzene copolymer.

4. Process according to claim 1, wherein the contact of the DMSO to be purified with the exchange resins takes place at a temperature of 19 to 80° C.

5. Process according to claim 4, wherein the temperature is between 20 and 50° C.

* * * * *